United States Patent [19]

Jacobs

[11] Patent Number: 4,849,447
[45] Date of Patent: Jul. 18, 1989

[54] ZEARALANOL DERIVATIVES WITH ANABOLIC ACTIVITY

[75] Inventor: Martin J. Jacobs, Terre Haute, Ind.

[73] Assignee: Pitman-Moore, Inc., Terre Haute, Ind.

[21] Appl. No.: 108,539

[22] Filed: Oct. 13, 1987

[51] Int. Cl.$^4$ ............... A61K 31/335; C07D 313/00
[52] U.S. Cl. ............................... 514/450; 549/270
[58] Field of Search ..................... 549/270; 514/450

[56] References Cited

U.S. PATENT DOCUMENTS

| | | | |
|---|---|---|---|
| 3,373,037 | 3/1968 | Abbott et al. | 549/270 |
| 3,373,038 | 3/1968 | Hodge et al. | 549/270 |
| 3,373,039 | 3/1968 | Hodge et al. | 549/270 |
| 3,887,583 | 6/1975 | Wehrmeister et al. | 549/270 |
| 3,957,825 | 5/1976 | Urry et al. | 549/270 |
| 4,024,602 | 8/1977 | Robertson et al. | 549/270 |
| 4,148,808 | 4/1979 | Hodge | 549/270 |
| 4,239,772 | 12/1980 | Shipchandler | 549/270 |
| 4,443,470 | 4/1984 | Hodge et al. | 549/270 |

OTHER PUBLICATIONS

Chemical Abstracts, vol. 69, No. 23, 96508v.

"Biodegradable Drug Delivery Systems", Wood, David A., Int. J. Pharm., 7, 1-18 (1980).
"Zearalenones: Characterization of Estrogenic Potencies and Receptor Interations of a Series of Fungal Beta-Resorcylic Acid Lactones", Katzenellenbogen et al., Endocrinology, 105: 33, 1979.

*Primary Examiner*—Mary C. Lee
*Assistant Examiner*—J. Richter
*Attorney, Agent, or Firm*—Wendell Ray Guffey; Thomas L. Farquer; Joseph M. Skerpon

[57] ABSTRACT

Compounds having the formula:

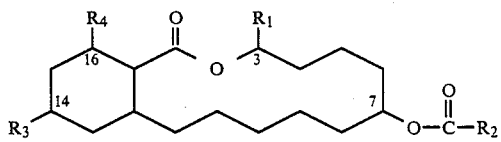

wherein $R_1$ is hydrogen, or an alkyl from about 1 to about 3 carbon atoms; $R_2$ is hydrogen, or an alkyl from about 1 to about 18 carbon atoms; $R_3$ is keto, or hydroxyl; and $R_4$ is hydrogen, an alkyl from about 1 to about 4 carbon atoms, hydroxyl, or amino are synthesized and administered to animals as anabolic agents.

13 Claims, No Drawings

ZEARALANOL DERIVATIVES WITH ANABOLIC ACTIVITY

FIELD OF THE INVENTION

This invention is directed to new compounds having anabolic activity in animals, processes of making these compounds, and methods of using these compounds.

BACKGROUND OF THE INVENTION

Over the years, anabolic agents have been heavily used as an aid in increasing the rate of growth in meat-producing animals. However, a drawback of such previously used compounds is that in addition to their anabolic activity, they possess some degree of hormonal activity. As a consequence, animals treated with these compounds tend to produce relatively high levels of fat as compared to the amount of muscle. Thus, while the early anabolic compounds may have achieved some degree of success in terms of weight gain, their hormonal properties resulted in weight gain which was of little economic value since a significant portion was due to the presence of fat.

In recent years, further concern has arisen over the use of these compounds in animals due to the possible estrogenic effect of these compounds on humans consuming the meat of these animals. As a result of this concern, one such common agent, diethylstilbestrol, is no longer sanctioned for use in animals in order to prevent entry of these compounds into the human food chain.

Another disadvantage of many anabolic compounds is that they often possess anti-bacterial activity. As a result, their use in animals may have a side affect wherein the natural balance of bacterial flora of the animal is disrupted. Such a change in the bacterial flora could be especially significant in ruminant animals where these compounds may disrupt the delicate ecological balance of bacterial flora in the rumen needed to insure the health and well being of the animal.

As a result of the many side effects associated with these early compounds there is a need for new anabolic compounds which lack undesirable hormonol activity.

SUMMARY OF THE INVENTION

It is an object of the present invention to provide new compounds having anabolic activity in animals.

It is an additional object of the present invention to provide new compounds having anabolic activity with low hormonal activity.

It is a further object of the present invention to provide a process for synthesizing the new compounds.

It is an additional object of the present invention to provide compositions useful in producing anabolic activity in animals.

It is another object of the invention to provide a method of increasing the anabolic metabolism of an animal.

In accordance with this invention there is provided anabolic compounds of the formula:

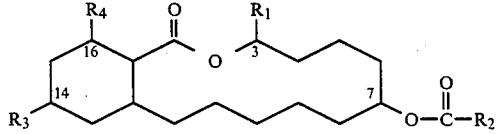

Wherein $R_1$ is hydrogen, or lower alkyl; $R_2$ is hydrogen, or an alkyl; $R_3$ is keto, hydroxyl, ketal, or ester; and $R_4$ is hydrogen, lower alkyl, amino, or hydroxyl.

In another embodiment, this invention provides compositions containing the compound of the invention useful in inducing anabolic metabolism in animals. In a further embodiment of the invention, a method of inducing anabolic metabolism in animals is provided using the claimed compounds. The invention also contemplates a method of making the claimed compounds.

The compounds of the present invention provide effective means of inducing anabolic metabolism in animals. Moreover, these compounds are relatively non-hormonal and possess little antimicrobial activity.

The compounds of the invention represent a significant advance in the science of anabolic agents. Although anabolic agents were known, these prior art compounds had significant side effects associated with them. For example, prior art compounds, in addition to being anabolic are also estrogenic and, often, are associated with an increased risk of cancer. As a result, animals treated with these prior art compounds tend to be obese, more prone to develop tumors, and to develop accentuated secondary sex characteristics such as pendulous mammary glands and enlarged genitalia. Understandably, considerable public concern has arisen as to the introduction of these anabolic compounds into the human food chain.

Another major drawback of prior art anabolic compounds is that many also possess antimicrobial activity which may cause an imbalance in the normal gut flora of the animal. This affect is particularly significant in ruminant animals, such as cattle and sheep, where the proper environmental balance of microorganisms in the rumen is essential to ensure the proper health and growth of the animal. The maintenance of a proper balance is important since these rumen microorganisms play a major role in allowing the animal to assimilate and break down cellulose as well as other components present in the animal diet. In contrast to the prior art anabolic compounds, the compounds of the invention show anabolic activity, but no apparent hormonal or antimicrobial activity. Thus, animals administered the compounds of the invention display weight gain in the absence of the significant side effects commonly found associated with the administration of prior art anabolic compounds.

DESCRIPTION OF THE PREFERRED EMBODIMENTS

The anabolic compounds of this invention have the formula:

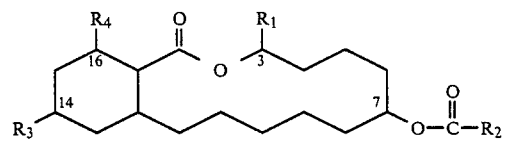

Wherein $R_1$ is hydrogen, or lower alkyl; $R_2$ is hydrogen, or an alkyl; $R_3$ is keto, hydroxyl, ketal, or ester; and $R_4$ is hydrogen, lower alkyl, amino, or hydroxyl.

Preferred compounds are those in which $R_1$ is hydrogen, or an alkyl from about 1 to about 3 carbon atoms; $R_2$ is hydrogen, or an alkyl having from about 1 to about 18 carbon atoms; $R_3$ is keto, or hydroxyl; and $R_4$ is hydrogen, an alkyl from about 1 to about 4 carbon atoms, or amino. A particularly preferred compound of the present invention is 7-acetoxy-hexahydrodideoxyzearalan-14-one.

The compounds of the present invention can be produced from the known compound, alpha-zearalanol:

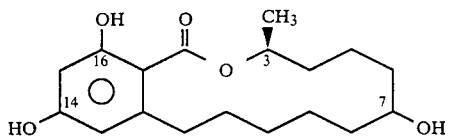

or its appropriate derivatives.

The compounds of the invention preferably begin with alpha-zearalanol and proceed such that the 16-hydroxyl group is eliminated. This elimination is carried out by selectively catalytically hydrogenating an intermediate compound. In order to accomplish this it is desirable to first protect the 14-hydroxyl group. It is also desirable, in a preferred embodiment, to esterify the 7-hydroxyl before this first hydrogenation. By first esterifying the 7-hydroxyl the product yield of the compounds of the invention are increased.

After elimination of the 16-hydroxyl group the compound is catalytically hydrogenated to saturate the aromatic ring. In a preferred embodiment, the 14-hydroxyl group is converted to a ketone.

Preparation of the compounds of this invention from alpha-zearalanol is preferably achieved by first protecting the 7-hydroxyl group by esterification. The esterification of this hydroxyl group can be performed by reacting zearalanol with an aliphatic acid up to about 20 carbon atoms in length. Preferred, are aliphatic acids having from about 1 to about 6 carbon atoms. Alternatively, esterification in position 7 can be carried out using aromatic acids such as, for example, benzoic and toluic acids. This reaction can be carried out in the presence of a catalytic amount of an inorganic acid such as, for example, sulfuric, hydrochloric or para-toluene sulfonic acids. Preferred as an acid catalyst is sulfuric acid.

After the 7-hydroxyl group has been protected, it is then preferable to protect the 14-hydroxyl group. Protection at this position is desirably obtained by formation of an ether. A preferred agent is benzyl chloride. This reaction can be carried out in the presence of potassium carbonate and methyl ethyl ketone (MEK). Protection can also be carried out, for example, by using the tetrahydropyranal derivative or alkyl groups of one or more carbon atoms in length.

Etherification of the 16-hydroxyl group is desirable and is preferably accomplished by the addition of chloro-phenyl-tetrazole. Other compounds useful in this reaction are benzoxazoyl chloride and methanesulfonyl chloride. This reaction can be carried out in the presence of potassium carbonate under refluxing conditions.

Removal of the oxygen from position 16 can be preferably accomplished by hydrogenation over palladium on carbon as catalyst. Other catalysts which can also be used are Raney nickel, platinum, ruthenium, and rhodium. The product of this reaction is 2-deoxy-alpha-zearalanol-6'-acetate.

Alternatively, the compounds of the invention can be synthesized from alpha-zearalanol by first protecting the 14-hydroxyl group by forming an ether bond at this position. The product of this reaction is then reacted with a compound to etherify the 16-hydroxyl group, before removal of oxygen from this position by hydrogenation. After this step the 7-hydroxyl group is protected by esterification. In general, each of these steps can be accomplished as described previously in the preferred method of synthesis.

The compound 2-deoxy-alpha-zearalanol-6'-acetate can also be produced as disclosed in U.S. Pat. No. 3,887,583.

Catalytic hydrogenation is employed to saturate the aromatic ring of 2-deoxy-alpha-zearalanol-6'-acetate. The saturation of the aromatic ring can be advantageously accomplished using rhodium on alumina in a hydrogen atmosphere. Other catalysts which can also be used are palladium, Raney nickel, and platinum.

After saturation of the aromatic ring, the hydroxyl group at position 14 is converted to a ketone for the preferred embodiment of this invention. This conversion is preferably accomplished by the addition of the Jones reagent which consists primarily of chromic acid, sulfuric acid and water. Alternatively, the oxidation of the hydroxyl group to a ketone can be accomplished through the use of other agents such as, for example, meta-chloroperoxybenzoic acid or sodium hypochlorite. Other oxidizing agents are useful and known to those of skill in the art.

The separation of the various isomers of the compounds of the invention can be done by chromatography. A preferred separation technique is column chromatography either with or without pressure.

The compounds of this invention are useful in inducing anabolic metabolism in ruminant as well as non-ruminant animals. Because of their effect on the metabolism, these compunds are capable of causing an animal to gain more weight when fed a given amount of food as compared to animals not receiving the compound of the invention that receive the same amount of food. In other words, animals receiving the compounds of the invention display an improvement in feed efficiency such that the number of pounds of feed needed to give a pound of weight gain is less when the animal is administered the compounds of the invention.

Generally, the dosage for the administration of the compounds of the invention will vary with the type of animal, the weight and age of the animal, and the particular compound which is used. The determination of the proper dosage to enhance weight gain in light of these variables is within the control and competence of one skilled in the art. Typically, dosage can vary from about 0.05 mg/animal/day to about 10 mg/animal/day, preferably from about 0.1 mg/animal/day to about 4.0 mg/animal/day, most preferably from about 2.0 mg/animal/day to about 4.0 mg/animal/day.

The compounds can be administered parenterally by subcutaneous, intramuscular or intravenous injection, nasopharyngeal or mucosal absorption, transdermal absorption, or by gradual perfusion over time. Examples of the manner in which gradual perfusion may be carried are by peristaltic means or using biodegradable matrix implants. (Wood, *International Journal of Pharmacy,* 7:1, 1980).

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyloleate. Aqueous carriers include water, alcoholic-aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers, such as those based on Ringer's dextrose, and the like. In addition, preservatives and other additives may also be present such as, for example, antimicrobials, anti-oxidants and the like.

The compounds of the invention can also be administered internally in feeds or separately. When administered separate from the animal feed the compound will usually be present in an oral composition.

Oral compositions may be in a liquid, lyophilized, or gel form. In solid dosage forms, the composition may comprise the compound of the invention together with a pharmaceutical carrier. The pharmaceutical carrier may be an aqueous or non-aqueous liquid or a solid. The composition may contain such inert diluents as sucrose, lactose, starch, or vermiculite as well as a lubricating agent. In the case of capsules, tablets and pills the composition may also comprise a buffering agent. Other forms for oral administration may also be prepared with an enteric coating which would prevent dissolution of the composition until reaching the intestines.

Liquid dosage forms for oral administration generally will comprise an enterically coated capsule containing the liquid dosage form of the composition. Suitable forms include emulsions, suspensions, solution and syrups containing inert diluents such as, for example, water, sugars polysaccharides, silica gels, gelatin, or alcohol.

A more complete understanding can be obtained by reference to the following specific examples which are provided for purposes of illustration only and are not intended to limit the scope of the invention.

EXAMPLE 1

A. Synthesis of 14-benzyl-alpha-zearalanol

A mixture of 5.0 g of alpha-zearalanol, 100 ml of isopropyl alcohol, 5.0 g of potassium carbonate (x1-½ $H_2O$) and 2.5 ml of benzyl chloride was allowed to reflux for 4 hours. The reaction mixture was cooled, filtered, and mixed with 50 ml of water to give 2.4 g. Recrystallization from 30 ml of isopropyl alcohol plus 20 ml of water followed by recrystallization from 30 ml of ethanol plus 15 ml of water gave 1.64 g of product (mp 129°–131° C.).

B. Synthesis of 14-benzyl-16-(5-phenyl-1H-2-tetrazolyl)-alpha-zearalanol

A solution of 14-benzyl-alpha-zearalanol (51.6 g, 0.125 moles) in 250 ml dry methyl ethyl ketone containing anhydrous potassium carbonate (35.0 g, 0.25 moles) is stirred at reflux while 5-chloro-1-phenyl-1H-tetrazole (33.9 g, 0.25 moles) was added all at once. The solution was allowed to reflux under nitrogen for 62 hours. The slurry was filtered, volatile material partially removed at the rotary evaporator, diluted with 200 ml methylene chloride, washed with water, dried over magnesium sulfate, filtered and stripped at the rotary evaporator to yield an oil. The oil was recrystallized twice from aqueous 3A-ethanol (2000 ml water/100 ml 3A-ethanol). This gave 47.6 g of white needles. (mp 121.5°–123° C.).

C. Synthesis of 16-deoxy-alpha-zearalanol

A solution of 14-benzyl-16(5-phenyl-1H-2-tetrazoyl)-alpha-zearalanol (33.5 g, 0.06 moles) in 1200 ml 3A-ethanol containing 10.0 g of 5% Pd/carbon (Aldrich) was warmed to 70°–75° C. under 500 psi of hydrogen pressure for 3.5-4.0 hours. At the end of this time, the slurry was cooled to room temperature and filtered to remove catalyst and concentrated to give 3.42 g of crude 16-deoxy-alpha-zearalanol whose $^1$H-NMR shows the presence of 5-phenyl-1H-2-tetrazolone.

The crude product was purified by column chromatography on silica to give after recrystallization from ethyl acetate 9.1 g (50% yield) of light yellow solid (mp 181°–183° C.).

D. Synthesis of 16-deoxy-alpha-zearalanol-7-acetate 16-deoxy-alpha-zearalanol (3.0 g, 0.01 moles) was added to 24 ml of glacial acetic acid containing 0.1 ml of concentrated $H_2SO_4$ (96%). This solution was warmed to 65°–72° C. and held at this temperature range for 4.0 hours. During this time, the 16-deoxy-alpha-zearalanol dissolved. At the end of the heating period, the solution was cooled to room temperature using a cold water bath and the clear, colorless solution allowed to stand undisturbed for 18 hours. During this time no crystals formed. The solution was poured into 1,000 ml $H_2O$ and a sticky solid obtained by suction filtration.

Column chromatography (150 g silica gel, 35% EtOAc/hexane at 15 ml/min) gave 3.21 g (Rf=0.30) of colorless viscous oil whose $^1$H-NMR (CHCl$_3$) gave: 7.75 delta (apparent trpilet, 2H, 1H aromatic and 1H phenolic OH which exchanges with $D_2O$); 6.74 delta (multiplet, 2H, aromatic); 5.36 delta (multiplet, 1H, 6' methine); 4.91 delta (multiplet, 1H, 10' methine); 2.5–3.5 delta (very broad doublet, 2.2H, benzylic), 2.08 delta (singlet, 3H, acetyl); 1.40 delta (broad multiplet, 14H, methylene); 1.36 delta (doublet, 3H, methyl (J=6.0 Hz)). A mass spectrum (EI) gave m/e 348 (M); m/e 330 (M—$H_2O$); m/e 288 (M—HOAc); m/e 270 (M—HOAc, —$H_2O$).

E. Synthesis of Hexahydro-16-deoxy-alpha-zearalanol-7-acetate 16-deoxy-alpha-zearalanol-7-acetate (3.12 g, 0.0090 moles) in 300 ml 3A-ethanol containing 1.5 g 5% rhodium/carbon (Aldrich) was added to a Parr pressure reactor, pressurized to 500 psi hydrogen and stirred at 400 rpm for 4.0 hours at 40° C. At the end of his time the reaction mixture was cooled to room temperature, contents suction filtered through 25 g of Filter Aide ® and the filter cake washed with 3A-ethanol (2×50 ml). The filtrate was stripped in a rotary evaporator to yield 2.76 g of colorless oil. The $^1$H-NMR (CDCl$_3$) gave: 4.97 delta (multiplet, 2H, 6' and 10' methine), 3.70 delta (broad multiplet, 2H, 4 methine and OH group (the integration for this region reduces by 1 proton when $D_2O$ is added and spectrum remeasured)); 2.65 delta (broad multiplet, 1H, 1 methine); 2.01 delta (singlet, 3H, acetyl); 1.1–2.1 delta (broad multiplet, 26H, methylene and methyl). The mass spectrum (EI) gave: m/e 354 (M), m/e 336 (M—$H_2O$), m/e 294 (M—HOAc), m/e 276 (M—HOAc, —$H_2O$).

F. Synthesis of 7-acetoxy-hexahydrodideoxyzearalan-14-one

A solution of hexahydro-16-deoxy-alpha-zearalanol-7-acetate (3.78 g, 0.0107 moles) in 150 ml of ethyl acetate was stirred while tetrabutyl ammonium bisulfate (0.50 g, 0.00147 moles) was added along with 150 ml of Chlorox ® bleach (2.66% w/w NaOCl, density 1.06 g/ml; 4.23 g NaOCl, 0.0568 moles). This mixture was stirred vigorously for 7.0 hours. At the end of this time the layers were separated, the lower phase was washed with EtOAc (2×50 ml) and organic phases combined, washed with $H_2O$ (2×50 ml), dried, filtered, and stripped to yield a colorless oil whose $^1$H-NMR was consistent with the product of the invention. The TLC (30% acetone/hexane) shows two of the four spots in the starting O[4]-alcohol are now at higher Rf's.

G. Isolation of 7-acetoxy-hexahydrodideoxyzearalan-14-one Isomers

Crude product (2.47 g) was subjected to flash chromatography using 25% EtOAc/pet. ether as solvent. This gave three fractions upon removing solvent at the rotary evaporator:
A. 0.63 Rf 0.28
B. 0.35 g Rf 0.32
C. 0.38 Rf 0.52 (broad)

FRACTION A

The crude oil representing this fraction was recrystallized from 25% acetone/hexane (10 ml/g) to give 0.38 g of white solid (mp 134°-135° C., uncorrected) and 0.12 g of yellow oil from the mother liquor. The $^1$H-NMR (CDCl$_3$) gave: 5.00 delta (broad multiplet, 1H, ester methine); 2.95 delta (broad multiplet, 1H, Cl methine); 2.01 delta (singlet, 3H, acetyl); 1.27 delta (doublet, (J=6.0 Hz), 3H, methyl); 2.70-1.0 delta (broad multiplet, 23H, methylene). The $^{13}$C-NMR (CDCl$_3$) (ppm) 210.1 (ketone); 173.2, 170.4 (acetate, lactone); 73.3, 69.6 (C—OR); 44.3, 44.2, 39.1, 38.8, 35.1, 29.9, 29.1, 27.6, 26.0, 24.9, 23.8, 21.2, 20.6, 20.2, 18.4. The FT-IR (thin film) gave 2942, 2865.8 cm$^{-1}$ (CH), 1725 (ketone, lactone, ester). The mass spectrum (EI) gave: 352 m/e (M); 324 m/e (M—CO); 309 m/e (M-acetyl).

Elemental analysis calculated for a compound having the formula $C_{20}H_{32}O_5$ was: C, 68.15%; H, 9.15%; O, 22.70%. Analysis of the material of fraction A showed that it contained: C, 68.11%; H, 9.13%; O, 22.94%.

FRACTION B

The crude oil was recrystallized from 15% acetone/hexane to give 0.080 g of white solid (mp 78°-81° C., uncorrected) and 0.24 g of oil from the mother liquor. The $^1$H-NMR (CDCl$_3$) gave: 5.02 delta (broad multiplet, 2H, ester methine); 2.99 delta (broad multiplet, 1H, Cl methine); 2.01 delta (singlet, 3H, acetyl); 1.28 delta (doublet (J=6.0 Hz), 3H, methyl); 1.85-0.9 delta (broad multiplet, 23H, methylene). The $^{13}$C-NMR (CDCl$_3$) gave (ppm): 210.0 (ketone); 173.4, 170.5 (acetate, lactone); 73.1, 71.3, (C—OR); 45.8, 45.2, 39.5, 35.9, 30.8, 28.7, 28.6, 26.0, 24.8, 23.7, 21.3, 20.9, 20.2, 19.9. The FT-IR (thin film) gave: 2946, 2923, 2877, 2857 cm$^{-1}$ (CH); 1711 cm$^{-1}$ (C=O). The mass spectrum (EI) gave: 352 m/e (M); 324 m/e (M—CO); 309 m/e (M-acetyl).

It was calculated that elemental analysis for a compound having the formula $C_{20}H_{32}O_5$ would have the following composition: C, 68.15%; H, 9.15%; O, 22.70%. Actual values determined for the compound of fraction B was: C, 67.89%, H, 9.13%, O, 23.04%.

FRACTION C

The crude oil of this fraction would not crystallize despite repeated attempts. The $^{13}$C-NMR spectrum of this material showed that at least two and possibly four components were present. The mass spectrum (EI) gave 326 m/e which was not consistent with the anticipated product.

EXAMPLE 2

A. Synthesis of Alpha-zearalanol-7-acetate

A mixture of 400 g alpha-zearalanol, 4 ml conc H$_2$SO$_4$ and 4 liters glacial acetic acid were added to a flask equipped with stirrer, condenser and thermometer. The reaction mixture was heated at 70°-75° C. for 7 hours. Contents were allowed to cool to room temperature overnight. White crystals were removed by vacuum filtration and dissolved in 7600 ml hot 3A-ethanol. After cooling to room temperature the resulting white crystals were removed by vacuum filtration. The crystals were air dried for about 48-72 hours. Net weight was 379 g, mp 122°-26°. An additional 27 g of crystals were recovered from the 3A mother liquor to give a total yield of about 406 g or 81% based on the starting weight of alpha-zearalanol.

B. Synthesis of 14-benzyl-alpha-zearalanol-7-acetate

A solution containing 1220 g (2.92 mole) alpha-zearalanol-7-acetate, 481 g (3.80 mole) benzyl chloride (99.9%), 1200 g (8.68 mole) anhydrous potassium carbonate and 8 liters methyl ethyl ketone (MEK) was added to a flask equipped with mantle, stirrer and two reflux condensers. The contents were heated to reflux and held for 71 h. Progress of the reaction was monitored by TLC on silica plates. Reflux was continued until essentially all of the zearalanol-7-acetate had reacted. The reaction mixture was cooled and the inorganic solids were removed by filtration and washed wih 300 ml MEK. The MEK reaction solution and wash were concentrated and filtered in several stages to give a total of 954 g crude product. Recrystallization from 3A ethanol 6:1 (vol/wt) gave 769 g product analyzing 97-98% by HPCL. A reverse phase column was eluted with 90:10 acetonitrile:water with U.V. detection at 254 nm. Approximate yield of product was 775 g or about 58% based on the starting weight of alpha-zearalanol-7-acetate.

C. Synthesis of 14-benzyl-16-(5-phenyl-1H-2-tetrazolyl)-alpha-zearalanol-7-acetate Methyl ethyl ketone (8 liters), 780 g (1.71 mole), 14-benzyl-alpha-zearalanol-7-acetate, 403 g (2.23 mole) 5-chloro-1-phenyl-1H-tetrazole and 478 g (3.46 mole) anhydrous potassium carbonate were added to a 12 liter reflux flask equipped with mantle, stirrer and two reflux condensers. The contents were allowed to reflux for a total of 63 hours. Progress was monitored by TLC on silica and by reverse phase HPCL eluted with 90:10 acetonitrle-water.

The major portion of MEK solvent was allowed to evaporate at room temperature in the hood. The resulting semi-solid mass was transferred to a 3 liter resin flask and vacuum stripped on a steam bath with a nitrogen purge at pump vacuum for 11 hours. The weight of the stripped material was 1090 g.

The 1090 g of crude product was divided into four approximately equal portions and each was dissolved in 300 ml 3A ethanol. The ethanol solutions deposited white needles after several hours stirring at room temperature. The needles were filtered and triturated with three times their dry weight 3A ethanol (v/wt). The resulting crystalline solids were filtered and dried. The total amount of dry crystalline product weighed 823 g (1.38 mole) which was 81% of the starting weight of 14-benzyl-alpha-zearalanol-7-acetate.

D. Synthesis of 16-deoxy-alpha-zearalanol-7-acetate

A total of 983 g 14-benzyl-16-(5-phenyl-1H-2-tetrazolyl)-alpha-zearalanol-7-acetate was hydrogenated over palladium on carbon catalyst. A total of 13 runs in a 2 liter Parr autoclave were carried out. A typical run is described below. Earlier runs were charged with 60 g 14-benzyl-16-(5-phenyl-1H-2-tetrazolyl)-alpha-zearalanol-7-acetate while later runs were charged with 120 g per run.

Typically, the hydrogenation was carried out at 80° C., 500 psig hydrogen for five hours. The catalyst was removed by filtration and ethanol was stripped on a rotary evaporator to leave 98.6 g solids.

The crude product from the reaction was triturated with carbon tetrachloride (5:1 v/wt) and filtered through a fine porosity pressure filter to remove phenyl tetrazolinone by-product. The resulting material contained approximately 88% 16-deoxy-alpha-zearalanol-7-acetate and 12% phenyl tetrazolinone. For the conversion of 16-deoxy-alpha-zearalanol-7-acetate to hexahydro-16-deoxy-alpha-zearalanol-7-acetate it is necessary to remove all but 1-2%, of the phenyl tetrazolinone. This was accomplished by flash chromatography.

E. Synthesis of Hexahydro-16-deoxy-alpha-zearalanol-7-acetate

A mixture of 20 g 16-deoxy-alpha-zearalanol-7-acetate, 4 g of 5% rhodium on alumina catalyst and 1 liter 3A ethanol were added to a 2 liter high pressure stirred reaction apparatus, pressurized to 1000 psi with hydrogen gas. The contents were heated to 60° C. and agitated for four hours maintaining temperature and pressure at 1000 psi. At the end of this time reactor contents were cooled to room temperature, catalyst removed by filtration and solvent removed at the rotary evaporator. The residual oil was pumped to constant weight with a vacuum pump operating at 0.2 mmHg. The viscous oil product was used directly in the next step.

F. Synthesis of 7-acetoxy-hexahydrodideoxy-zearalan-14one

Hexahydro-16-deoxy-alpha-zearalanol-7-acetate (15.0 g) was dissolved in 500 ml acetone and cooled to 0°-5° C. The Jones Reagent (134 g chromic acid in 115 ml conc $H_2SO_4$, q.s. to 500 ml with $H_2O$) is added dropwise until the initial green color changes to an orange brown color that persists for five minutes. The exact amount of Jones reagent will depend on the purity of the hexahydro-16-deoxy-alpha-zearalanol-7-acetate used. This can be easily determined by thin-layer chromatography (TLC). On the average, 17 ml of the Jones reagent was required. When reagent addition was completed, the reaction mixture was stirred for five minutes longer and 500 ml of water was added and the solution extracted with ethyl ether. The volatile components were removed from the combined extracts at the rotary evaporator. The viscous residue was pumped to constant weight at the vacuum pump to give 13.5 g of product which on HPCL analysis contained 30% of the desired isomer, 50% of the inactive isomer and the remainder being impurities. The two isomers were separated and purified as described above in Example 1, part G.

EXAMPLE 3

A. Anabolic Activity of 7-acetoxy-hexahydrodideoxyzearalan-14-one

The compound purified from Fraction B above (Example 1G) was tested in sheep to determine its anabolic activity. Sheep were daily injected subcutaneously with this compound and its anabolic activity compared to sheep receiving injections of diethylstilbestrol (DES) and placebo control animals receiving no anabolic compound. Periodically, over 10-14 days, blood samples were taken and blood urea nitrogen (BUN) determined. A compound which possesses anabolic activity will cause a decrease in BUN for the treated sheep relative to the placebo control injected sheep. The results of the study are shown in Table 1.

TABLE 1

IN VIVO ANABOLIC ACTIVITY OF 7-ACETOXY-HEXAHYDRO-DIDEOXYZEARALAN-14-ONE

| TREATMENT | BUN CHANGE[a] | | |
|---|---|---|---|
| | DAY 4 | DAY 8 | DAY 11 |
| DES | −2.18 | −4.53[e] | −3.48[d] |
| INVENTION[b] | | | |
| 0.1 | −1.66 | −0.93 | −0.70 |
| 0.4 | −0.90 | −1.01 | 0.95 |
| 2.0 | −2.21[c] | −1.16 | −1.45 |
| 4.0 | 0.10 | −2.10[c] | −2.00[c] |

[a] expressed as difference in BUN value as compared to placebo control animals.
[b] compound of Fraction B, Example 1 G in mg.
[c] $p < 0.10$
[d] $p < 0.05$
[e] $p < 0.01$ BUN's of animals receiving the compound of Fraction B were significantly lowered on day 4 at a dose level of 2.0 mg/animal/day, and on days 8 and 11 at dose levels of 4.0 mg/animal/day. This study confirms the BUN-lowering activity of the compound of the invention (Fraction B) and shows its efficacy as an anabolic agent.

The invention now being fully described, it will be apparent to one of ordinary skill in the art that many changes and modifications can be made without departing from the spirit or scope of the invention.

What is claimed is:

1. Anabolic compounds of the formula:

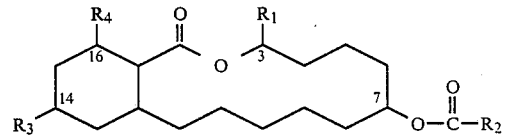

wherein $R_1$ is hydrogen, or an alkyl from about 1 to about 3 carbon atoms; $R_2$ is hydrogen, or an alkyk from about 1 to about 18 carbon atoms; $R_3$ is keto, or hydroxyl; and $R_4$ is hydrogen, an alkyl from about 1 to about 4 carbon atoms, hydroxyl, or amino, with the proviso that $R_3$ and $R_4$ cannot simultaneously be OH.

2. The compound of claim 1, which is 7-acetoxy-hexahydrodideoxyzearalan-14-one.

3. A method for increasing the anabolic metabolism in an animal which comprises administering to said animal an anabolically effective amount of a compound of the formula:

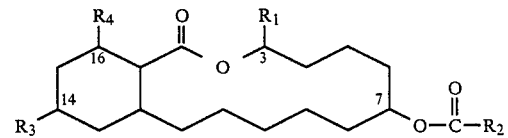

wherein $R_1$ is hydrogen, or an alkyl from about 1 to about 3 carbon atoms; $R_2$ is hydrogen, or an alkyl from about 1 to about 18 carbon atoms; $R_3$ is keto, or hydroxyl; and $R_4$ is hydrogen, an alkyl from about 1 to about 4 carbon atoms, hydroxyl, or amino.

4. The method of claim 3, which said compound is 7-acetoxy-hexahydrodideoxyzearalan-14-one.

5. The method of claim 3, wherein said compound is administered parenterally.

6. The method of claim 5, wherein said parenteral administration is by subcutaneous, intramuscular, or intravenous injection, nasopharyngeal or mucosal absorption, or transdermal absorption.

7. The method of claim 5 wherein said administration is by gradual perfusion.

8. The method of claim 7, wherein said gradual perfusion is by peristaltic means.

9. The method of claim 7, wherein said gradual perfusion is by use of a degradative matrix.

10. The method of claim 3, wherein said compound is administered internally.

11. The method of claim 3, wherein said compound is administered at a dose of from about 0.1 mg/animal/day to about 10 mg/animal/day.

12. The method of claim 3, wherein said compound is administered from about 0.1 mg/animal/day to about 4.0 mg/animal/day.

13. The method of claim 3, wherein said compound is administered from about 2.0 mg/animal/day to about 4.0 mg/animal/day.

* * * * *

UNITED STATES PATENT AND TRADEMARK OFFICE
CERTIFICATE OF CORRECTION

PATENT NO. : 4,849,447

DATED : July 18, 1989

INVENTOR(S) : Martin J. Jacobs

It is certified that error appears in the above-identified patent and that said Letters Patent is hereby corrected as shown below:

```
Column 5, line 29, "following the word "sugars" insert --,--
Column 6, line 40, "his" should read --this--
Column 8, line 28, HPCL" should read --HPLC--
Column 8, line 42, "HPCL" should read --HPLC--
Column 8, line 43, "acetonitrle" should read --acetonitrile--
Column 9, line 30, "-14ONE" should read -- -14-ONE --
Column 9, line 48, "HPCL" should read --HPLC--
Column 10, line 39, Claim 1, "alkyk" should read --alkyl--
Column 6, line 24, "trpilet" should read --triplet--
```

Signed and Sealed this

Second Day of October, 1990

Attest:

HARRY F. MANBECK, JR.

*Attesting Officer*     *Commissioner of Patents and Trademarks*